(12) United States Patent
North, Jr.

(10) Patent No.: US 6,624,621 B2
(45) Date of Patent: Sep. 23, 2003

(54) PARTICLE COUNTER VOLUME SENSOR

(76) Inventor: Howard L. North, Jr., P.O. Box 390, Oldwick, NJ (US) 08858-0390

( * ) Notice: Subject to any disclaimer, the term of this patent is extended or adjusted under 35 U.S.C. 154(b) by 74 days.

(21) Appl. No.: 09/746,762

(22) Filed: Dec. 22, 2000

(65) Prior Publication Data

US 2001/0052763 A1 Dec. 20, 2001

Related U.S. Application Data

(63) Continuation of application No. 09/746,762, filed on Dec. 22, 2000, now abandoned
(60) Provisional application No. 60/194,273, filed on Apr. 3, 2000.

(51) Int. Cl.$^7$ .............................................. G01N 27/00
(52) U.S. Cl. ..................................... 324/71.4; 324/453
(58) Field of Search ............................. 324/71.4, 71.1, 324/436, 453; 73/865.5, 861.41, 61.71

(56) References Cited

U.S. PATENT DOCUMENTS

| | | | |
|---|---|---|---|
| 2,656,508 A | 10/1953 | Coulter ....................... 324/71.1 |
| 6,111,398 A | * 8/2000 | Graham ....................... 324/71.4 |
| 6,175,227 B1 | * 1/2001 | Graham ....................... 624/71.4 |
| 6,228,652 B1 | * 5/2001 | Rodriguez et al. ............ 436/63 |
| 6,259,242 B1 | * 7/2001 | Graham ....................... 324/71.4 |

FOREIGN PATENT DOCUMENTS

| | | | |
|---|---|---|---|
| EP | 0 187 663 | * 7/1986 | ................. 324/71.4 |
| JP | 57-179729 | * 11/1982 | ................. 324/71.4 |

OTHER PUBLICATIONS

Spielman, Improving resolution in Coulter Counting by hydrodynamic focusing, J. Colloid Interface Sci. 26:175–182 (1968).

Thom, Fortschritte fuer die elektronische Grossenbestimmung von Blutkoerperchen, Blut 21:48–50 (1970).

V. Kachel, Flow Cytometry and Sorting, Ch.4, 1990, Wiley–Liss Electrical Resistance Pulse Sizing: Coulter Sizing.

Leif, Electronic cell–volume analysis by use of AMAC 1 transducer, Clin. Chem. 19:853–870 (1973).

Salzman, A Coulter volume spectrometer employing a potential sensing technique Biophys. Soc. Abstr. 17:302a (1973).

Karuhn Studies on Coulter Counter, Part I, Investigations into the effect of orifice geometry and flow direction on the measurement of particle volume, Powder Technol. 11:157–171 (1975).

Davies, Studies on the Coulter counter. Part II: Investigations into the effect of flow direction and angle of entry on a particle volume and pulse shape. Powder Technol. 12:157–166 (1975).

\* cited by examiner

*Primary Examiner*—Jay Patidar
*Assistant Examiner*—Walter Benson (57) ABSTRACT

A particle counter volume sensor for sensing by the electrical resistance puplse method the volume of particles in a fluid suspension passing through an orifice assembly which includes an orifice member made of electrically insulating material and electrically resistive material disposed before, within, and after the orifice. The orifice is cylindrical with well rounded entry and exit corners. The resistive material has a conduit for the passage of particles through it generally centered with the orifice. The resistive material has an electrical resistivity matching that of the particle suspending fluid. Thus the electric field within the orifice is substantially the same with or without the resistive material. The conduit restricts particles to trajectories through the orifice where the maximum electric field intensity is substantially uniform thus accurately sizing the particles. The conduit and resistive material prevent particles recirculating downstream from the orifice from passing through regions of significant electrical field strength thus avoiding particle volume sizing and counting errors. This particle counter volume sensor thus provides virtually all of the performance of orifices using front and rear sheath flows without the use of such sheath flows.

4 Claims, 6 Drawing Sheets

PARTICLE COUNTER VOLUME SENSOR

This is a continuation of application Ser. No. 09/746,762 filed Dec. 22, 2000, now abandoned.

This Application claims the benefit of Provisional Patent Application No. 60/194,273 filed Apr. 3, 2000.

BACKGROUND

1. Field of Invention

This invention relates to orifices used to electrically sense the volume of particles in a fluid suspension flowing through the orifice.

2. Description of Prior Art

This background is provided to clarify the problems solved and the improvements provided by my invention.

Figure 1:
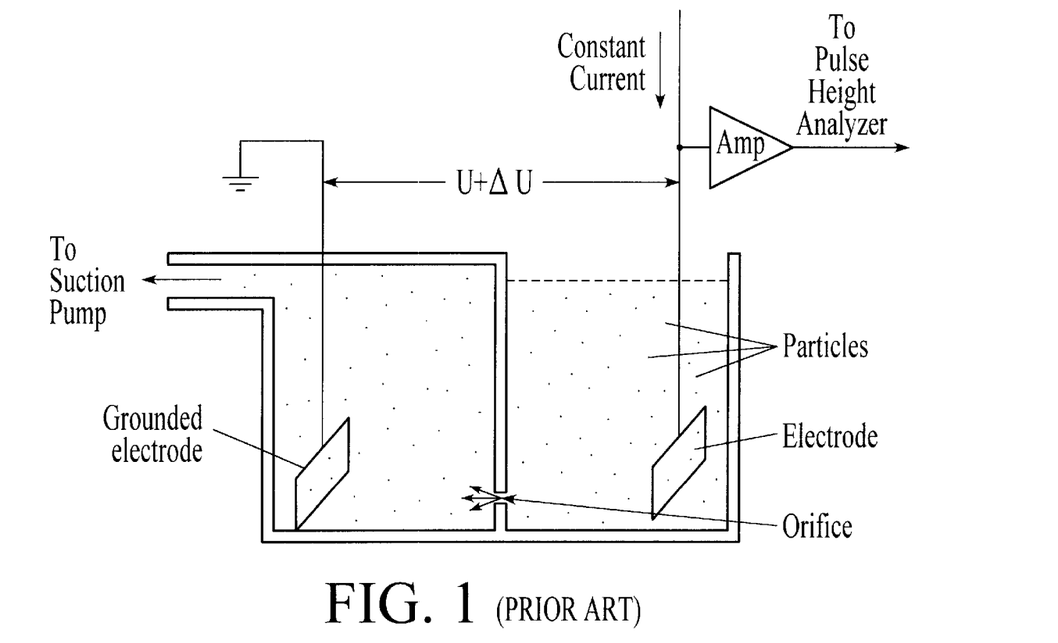
FIG. 1 (Prior Art) Shows the basic particle sensing orifice in an instrument.

In U.S. Pat. No. 2,656,508 issued in 1953 Coulter described his invention for a "Means for counting particles suspended in a fluid" which provided an entirely new method of blood cell counting and sizing that was automatic, accurate, and reliable. Coulter's idea was to pass-particles suspended in a conducting electrolyte through a small diameter orifice of short length. The electrical resistence of the particle must be greater than that of the electrolyte. A constant current was maintained across the orifice by two electrodes, one on each side of it. Then, as each particle traversed the orifice it displaced electrolyte, thereby producing an increase in resistance. This resistance pulse is observed as a voltage pulse. These voltage pulses are measured across the two electrodes, amplified, and those greater than a minimum or threshold value are counted with electronic scalers. FIG. 1 shows this basic resistance pulse device according to Coulter.

Coulter stated that the pulses are directly proportional to the volume of the particles, and thus the measured pulse height distributions should directly correspond to the volume distributions of the measured particles. However, this did not prove to be true. An excellent review of investigations into the causes for this discrepance and ways to eliminate or reduce it is presented by Volker Kachel in Chapter 4 of Flow Cytometry and Sorting, 2nd Edition, Wiley-Liss, 1990.

Two sources for the variable particle volume sensitivity have been identified. One is the non-uniform electrical field present within and adjacent to the orifice which produces electrical pulses of different heights and different time durations for particles of the same shape and volume which travel along different paths through the orifice. This effect is especially pronounced for particles traveling near entry and exit corners of the orifice where the electric field is concentrated and more intense.

A second source of volume signal error is produced by particles which have already passed through the orifice. These are present in the recirculating fluid at the downstream side of the orifice caused by the orifice effluent jet flow. When these particles pass near the exit corners of the orifice they produce pulses which are smaller in magnitude and longer in time duration than those produced by particles passing through the orifice.

Figure 2:
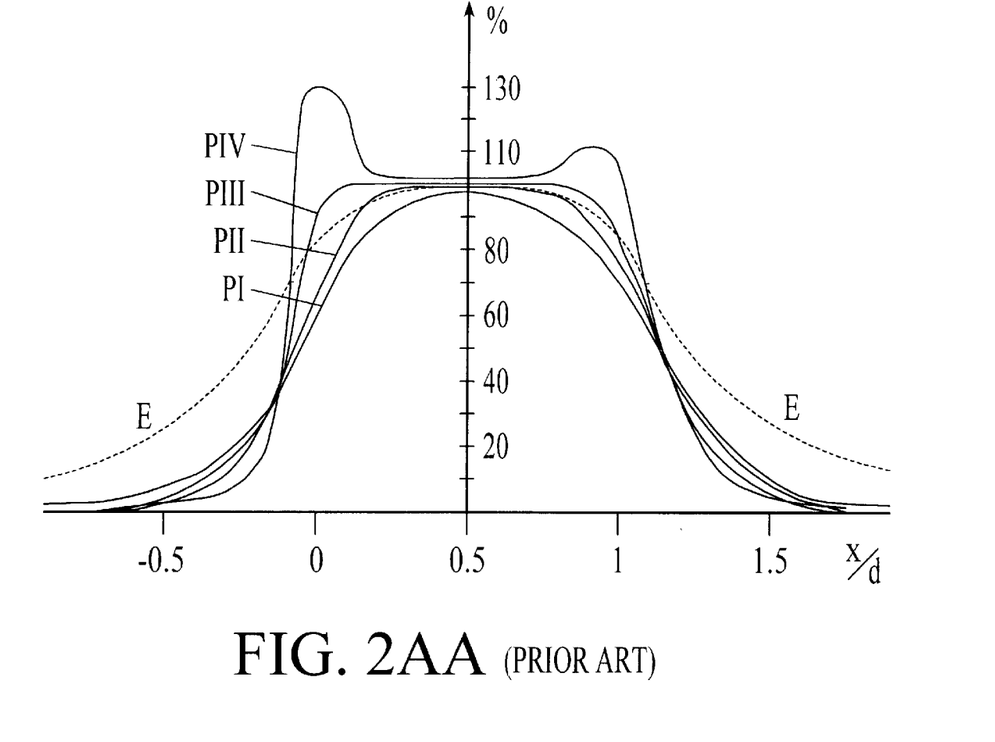
Figure 2A:
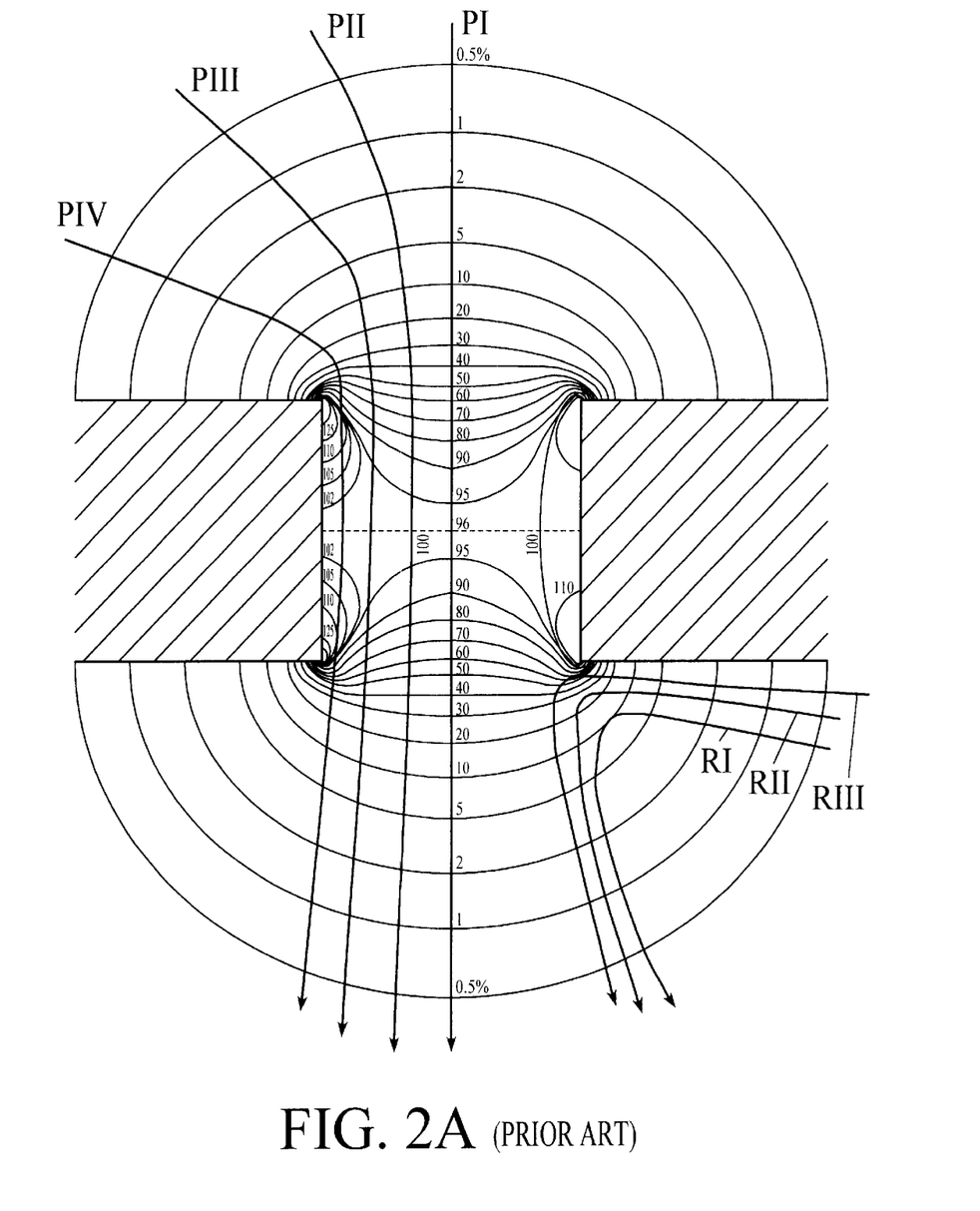
FIG. 2A (Prior Art) Shows the particle volume sensitivity within an orifice and also possible particle paths PI to PIV and recirculating particle paths RI to RIII.

The artifacts due to the non-uniform particle volume sensitivity of an orifice and the pulses produced by various particle paths through the orifice as well as those pulses produced by particles recirculating downstream of the orifice are shown on FIGS. 2(a), (aa), and (ab) respectively taken from the referenced work by Volker Kachel. It is clear that these artifacts can grossly distort the true particle volume distribution curves and true particle counts.

Figure 3:
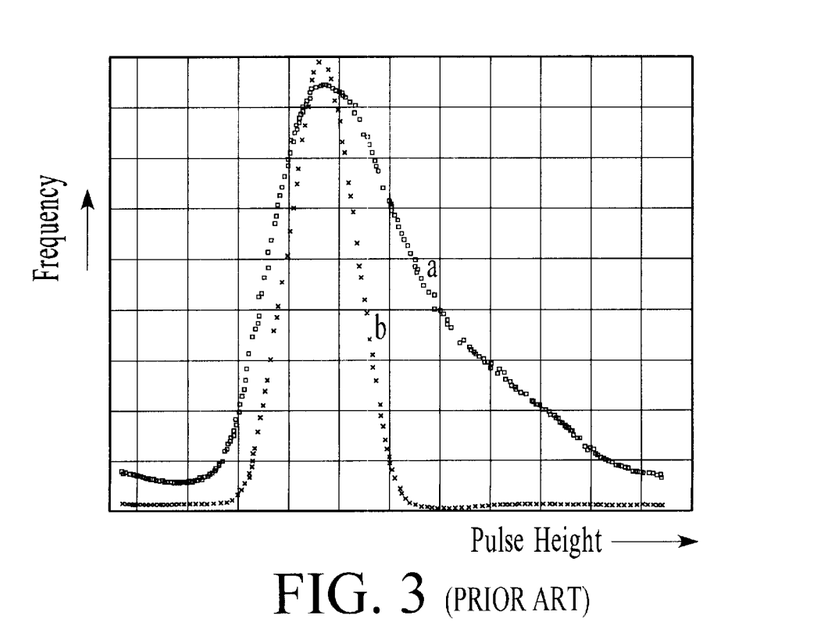
FIG. 3 (Prior Art) Shows the volume distribution curves of native erythrocytes with a Coulter counter (a) and with a focusing device (b).

Various means to reduce or eliminate these artifacts have been devised. Spielman in J. Colloid Interface Sci., 26:175–182, 1968 described use of hydrodynamic focusing to virtually eliminate the effects of non-uniform sensitivity within the orifice by use of a sheath flow of particle-free electrolyte to carry the sample suspension through the center of the orifice. This sheath flow rate is in the order of 100 times that of the sample suspension flow rate. Thus the diameter of the sample stream is about 10% of the orifice diameter. This results in all the particles passing through a region of highly uniform particle volume sensitivity. This resulted in the improvement in erythrocyte volume sizing accuracy shown in FIG. 3 taken from Thom and Kachel in Blut 21:48–50, 1970.

Figure 4:
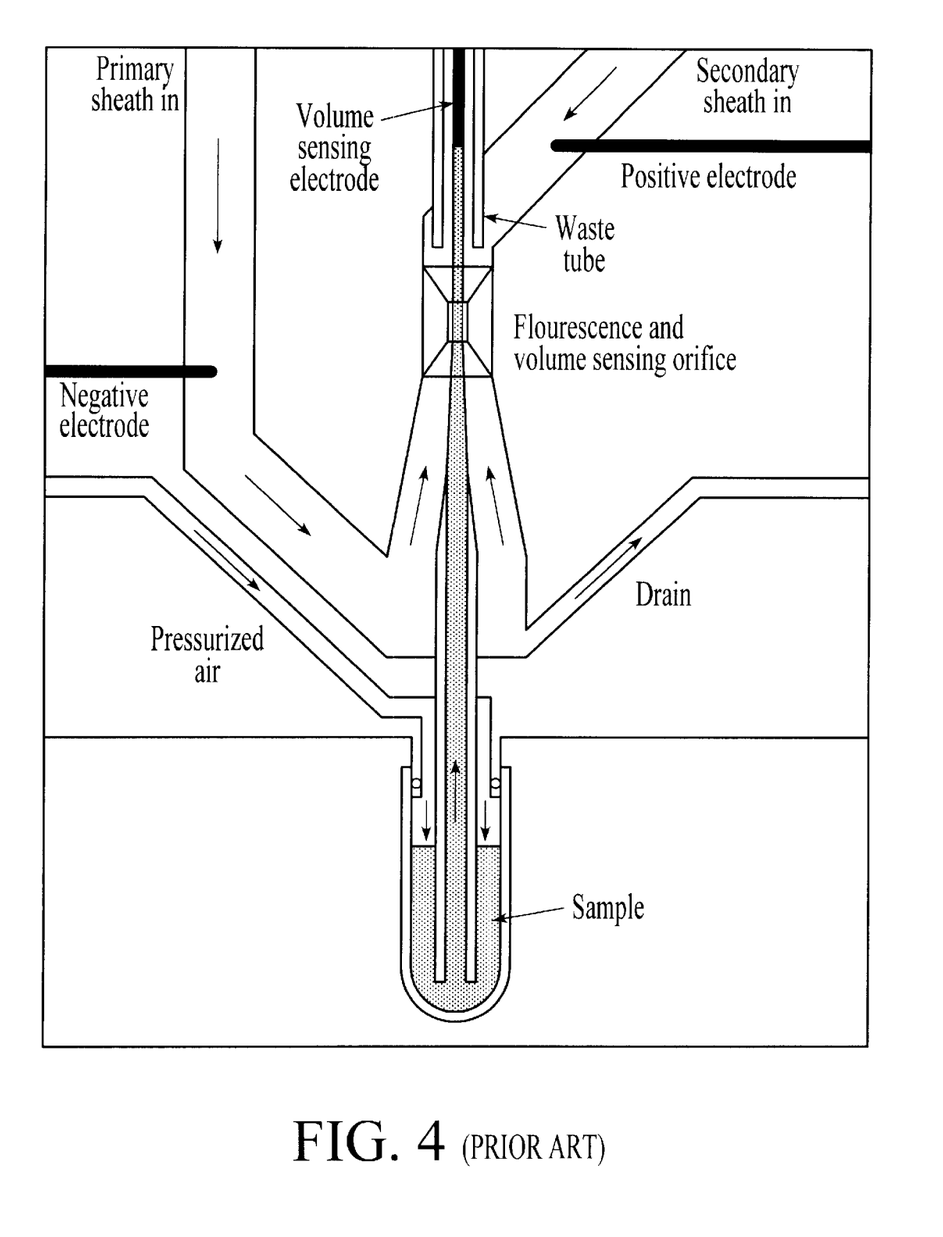
FIG. 4 (Prior Art) Fluidic paths for the Becton Dickinson FACS cell analyzer.

The artifacts due to particles recirculating immediately downstream of the orifice are totally eliminated by capturing the effluent jet in a catcher tube and flushing the exit zone of the orifice with a particle-free electrolyte which also exits via the catcher tube. This rear sheath flow eliminates the recirculating particles which are especially troublesome when sizing and counting both small and large particles simultaneously. An instrument for counting both platelets and erythrocytes which utilizes both front and rear sheath flows was described by Haynes in Blood Cells, 6: 201–213, 1980. FIG. 4 shows the fluidic design of another instrument utilizing front and rear sheath flows.

Figure 5:
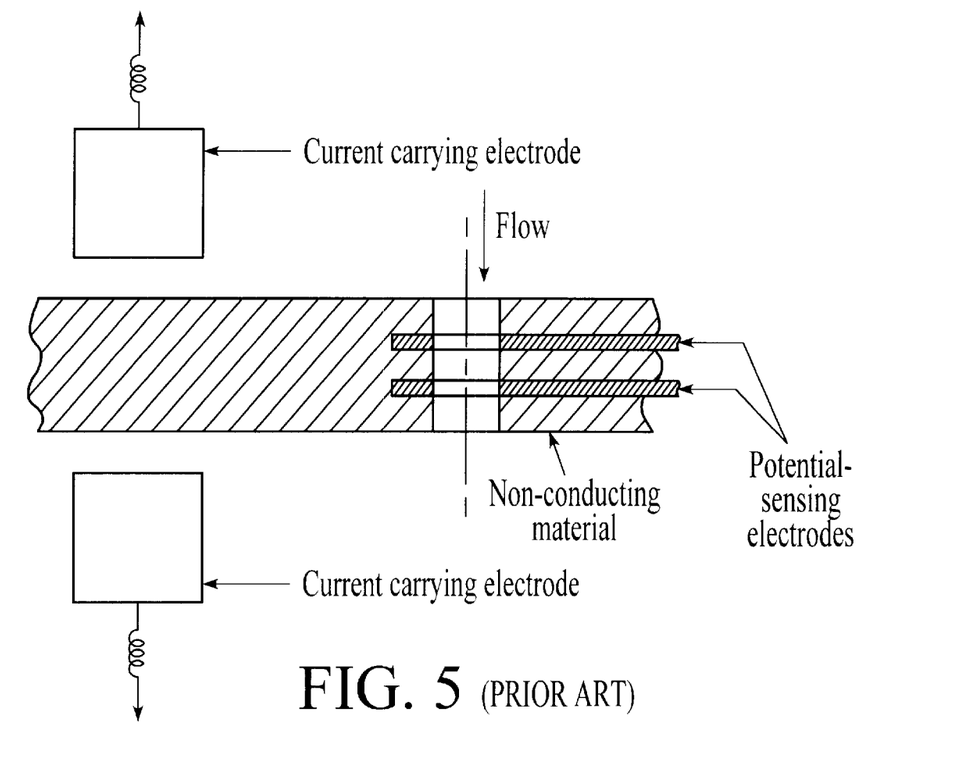
FIG. 5 (Prior Art) Orifice with embedded potential sensing electrodes.

FIG. 5 shows potential sensing electrodes located within the orifice itself in a zone having relatively uniform sensitivity and remote from recirculating particles. Leif and Thomas in Clin. Chem., 19:853–870, 1973 as well as Salzman et al in Biophys. Soc. Abstr., 17:3029, 1973 describe these orifices and their performance. This idea virtually eliminate particle volume centering artifacts and totally eliminates the recirculating particle artifact.

Karuhn et al in Powder Technol., 11:157–171, 1975 showed that an orifice without sharp corners greatly reduced the more intense electric field at the entry and exit corners of the orifice. Thus a rounded corner orifice substantially eliminates the non-uniform sensitivity artifact but does not eliminate the recirculating particle artifact.

Thr designs reviewed above all suffer from significant shortcomings. Front and rear sheath flow designs consume considerable quantities of special particle-free fluid which adds to the cost of operation as well as to the size and cost of the instrument system itself. It also adds to the cost of labor to fill the supply reservoirs, empty waste reservoirs, and dispose of large quantities of biohazardous waste fluid.

Designs using potential sensing electrodes within the orifice tend to be costly due to the difficulty of fabricating the orifice assembly itself. Also the design is not readily adaptable to the original Coulter volume sensing scheme having the orifice toatally immersed in electrolyte where the electrode leads must be well insulated from one another as well as the surrounding electrolyte and must have low interelectrode capacitance.

Designs using rounded corner orifice shapes are commonly used where only one population of particle sizes is to be encountered, such as erythrocytes or leukocytes. It can be fitted with rear sheath flow to eliminate recirculating particle artifacts to permit analyzing large and small particles simultaneously. However, this incurs the shortcomings due to use of sheath flows described above. Additionally, the rounded edge entrance tends to cause wedging of particles slightly larger than the orifice diameter which makes them more difficult to remove by wiping or reverse flushing than is true with sharp cornered orifices. Also partial clogs at the orifice inlet can cause significant changes in the orifice volume sensitivity.

My invention described herein provides the advantages and performance of orifices with front and rear sheath flow with none of their disadvantages.

OBJECTS AND ADVANTAGES

Several objects and advantages of the particle volume sensing orifice arrangement of the present invention are:

(a) to provide a particle volume sensing orifice arrangement with substantially uniform sensitivity to particle volume regardless of the path of the particle passing through the orifice;

(b) to provide a particle volume sensing arrangement free of substantial response to particles recirculating downstream of the orifice near the orifice exit;

(c) to provide a particle volume sensing orifice arrangement which achieves the objects of (a) and (b) without use of front or rear sheath flows;

(d) to provide a particle volume sensing arrangement which achieves the objects of (c) which can easily replace existing orifices;

(e) to provide a particle volume sensing orifice arrangement with sharp entry corners which is more resistant to particle clogging and which is more readily cleared of clogging particles by wiping or reverse flushing than an orifice with rounded entry corners;

(f) to provide a particle volume sensing orifice arrangement which is not substantially affected as regards its particle volume sensitivity by the presence of a partially clogging particle at the orifice inlet;

(g) to provide a particle volume sensing orifice arrangement which provides the foregoing advantages with only a small increase in manufacturing cost;

(h) to provide a particle volume sensing orifice arrangement which provides the foregoing advantages and is useable in existing instrument designs with only negligible instrument design changes.

Further objects and advantages will become apparent from a consideration of the ensuing description and drawings.

DRAWING FIGURES

FIG. 2AA (Prior Art) Shows the normalized voltage pulses produced by identical particles on paths PI to PIV, flow velocity neglected.

FIG. 2AB (Prior Art) Shows the normalized voltage pulses produced by identical particles on recirculating paths RI to RIII, one path PI, and a typical threshold level. Time axis is different from that of FIG. 2AA.

LIST OF REFERENCE NUMERALS

1—Electrically insulating material
2—Electrically resistive material

Description of Invention

Figure 6:
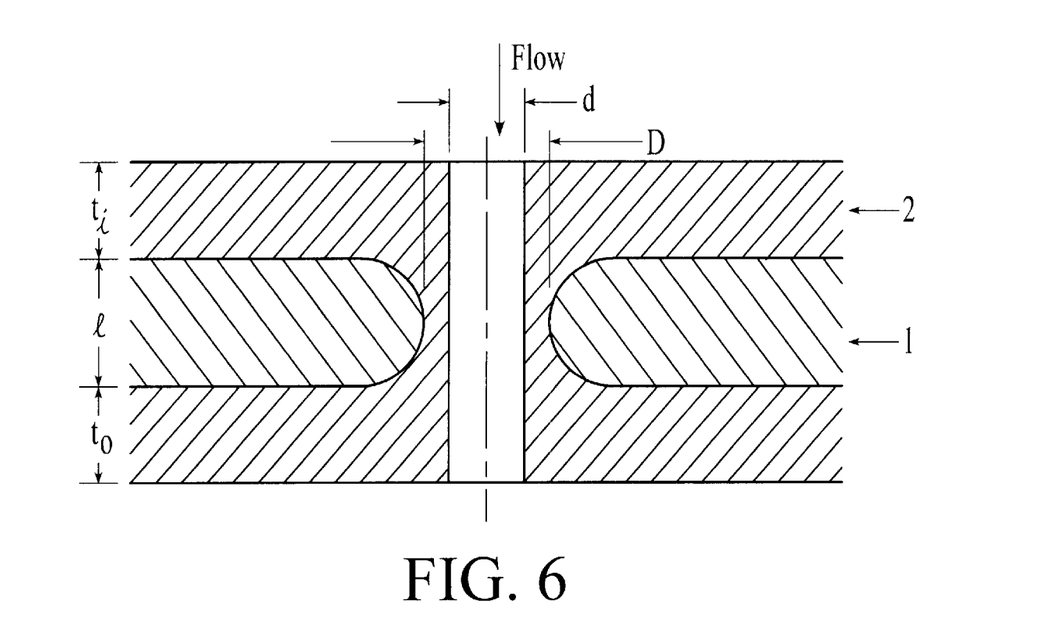
FIG. 6 Particle volume sensing orifice arrangement.

My invention is shown on FIG. 6. The electrically insulating material 1 orifice member has a diameter D, typically in the order of 100 micrometers, which has rounded entry and exit corners. This orifice without any electrically resistive material, would have a substantially uniform electric field at its minimum diameter D and would therefore produce good particle volume sensing for those particles passing through the minimum diameter zone. The presence of electrically resistive material 2 at the inlet to this orifice with a conduit having a diameter d, preferably smaller than D, causes the particle suspension to pass through a region of uniform electrical field. This is much like hydrodynamically focused particle suspension formed by front sheath flow. The electrically resistive material has a resistivity substantially the same as that of the electrolyte which for commonly used phosphate buffered saline is about 68 ohm cm at 25 C. Thus the electrically resistive material electrically replaces the electrolyte and produces negligible distortion of the electric field within the orifice. By making $t_1$ greater than D the presence of partially clogging particles at the entry to conduit d will exert a small effect on particle volume sensitivity.

The electrically resistive material on the exit side of the electrically resistive material orifice prevents recirculating particles from passing through significant electric fields and thus prevents the generation of pulses of objectionable magnitude when $t_2$ is greater than D. An orifice arrangement for analyzing human blood cells would have the following typical dimensions in micrometers: D=100, d=80, l=100, $t_1$=100, $t_0$=100. Adjustments to these dimensions will permit optimizing the design for specific applications.

Initially there was concern that the change in electrical conductivity from ionic in the electrolyte to electronic in the electrically resistive material would cause gas bubbles to be formed at the interface which would produce electrical pulses disturbing the particle volume sensing and counting functions. With saline the gas bubbles could be hydrogen or chlorine. A hydrogen ion, an atom of hydrogen with a positive electric charge, moves through an electrolyte to a negatively charged surface to produce a flow of current. Similarly, a chlorine ion, an atom of chlorine with a negative electric charge, moves through an electrolyte to a positively charged surface. Each ion yields its charge to the surface where the charge is carried away by electronic conduction. Each atom of hydrogen or chlorine is now without charge and joins with other identical atoms to form a diatomic gas. When the concentration of dissolved hydrogen or chlorine gas exceeds the solubility limit of that gas in the electrolyte at its temperature and pressure then gas bubbles can form on the electronically conducting material surface.

Besides dissolving of gas in the electrolyte several other factors inhibit the formation of gas bubbles. First, the hydrogen and chlorine atoms and molecules are constantly diffusing from the higher concentration at the electronically conductive material surface to the lower concentration electrolyte. This diffusion process is enhanced by electrolyte flow through the conduit of diameter d in the resistive material and also by the recirculating electrolyte flow at the downstream face of the resistive material. These flows act to remove hydrogen and chlorine gas dissolved in the electrolyte from the vicinity of the resistive material surface. This increases the concentration gradients for these gases, which in turn, increases the diffusion rates of these gases from the surface of the resistive material into the electrolyte. Since the upstream face of the resistive material has less vigorous flow of electrolyte it should be chosen as the surface on which chlorine gas tends to accumulate because chlorine gas has a much higher solubility in aqueous electrolyte than hydrogen gas. This means that the inlet electrode should be negative and the exit electrode should be positive.

Other factors which tend to inhibit the formation of gas bubbles at the interface between ionic conducting electrolyte and electronic conducting resistive material are an overvoltage needed to produce surface gas atoms and a concentration polarization which makes liberation of gas bubbles difficult. Taken together, all of these factors allow a bubble-free current of magnitude sufficient for some particle analyses for a period of time. This time period can be increased by periodically reversing the electric current or by fluid flow without electric current.

Fabrication of the Invention

There are several constructions described herein. Other constructions will occur to those skilled in the art. These will look like FIG. 7.

The first construction uses either p or n doped silicon having a resistivity substantially matching that of the particle suspending electrolyte. n doped silicon is less expensive and easier to work with than p doped silicon. If phosphorus is the dopant the concentration will be in the order of one atom of phosphorus per $2 \times 10^{15}$ atoms of silicon. Electrolyte commonly used for blood cell analysis is phosphate buffered saline having a resistivity of 68 ohm cm at 25 C. This doped silicon is placed in one of the cavities of an orifice member shaped like that of FIG. 7. The orifice member is made of an electrically insulating material having a melting point substantially higher than that of silicon. One suitable material for the orifice member is corundum which has a melting point of 2030 C. compared with 1420 C. for silicon. Both the orifice member and the doped silicon are heated to a temperature sufficient to melt the doped silicon causing it to wet and fuse to the corundum. Heating is done in an inert atmosphere furnace to prevent oxidation of the doped silicon which interferes with the wetting and fusing to the corundum. Pressure is applied to the molten silicon by gas or mechanical means to force some silicon through the hole in the orifice member and to fill the cavity on the opposite side. After annealing and cooling to room temperature excess silicon is removed by abrasive means to produce the shape shown on FIG. 7. The cylindrical aperture through the silicon may then be produced by excimer laser or other suitable means. Excimer lasers can produce accurate, round, straight-sided, uniform diameter holes with negligible spatter or undesirable thermal effects.

A specialty glass having significant electrical conductivity can be used in place of the doped silicon. Some glasses increase electronic conduction and reduce ionic conduction by reducing the amounts of sodium and calcium oxides and increasing the amounts of vanadium and phosphorus pentoxides. Electronic conduction can be further increased by adding large amounts of oxides that are semiconductors such as iron, cobalt, and manganese oxides. Another variety of conductive glasses contains the mixture $Na_2.B_2O_3.TiO_2$ and is used in thermistors. By these or similar techniques Corning Glass Company has achieved a resistivity of 6 ohm cm in their type 8830 glass. Glass would be processed similarly to doped silicon to produce the arrangement shown on FIG. 7.

Another construction uses small carbon particles dispersed in a rigid polymer matrix such as is used in carbon composition electric resistors. This carbon composition is molded in the orifice member and then the through aperture is formed, preferably by excimer laser to produce the arrangement shown on FIG. 7.

Another construction uses sputtering to deposit doped silicon from a source crystal onto an electrically nonconducting orifice. Sputtering produces strongly adherent films at close to room temperature conditions. After build up of sufficient film thickness the coated orifice member is finished by abrasive means to the shape of FIG. 7 and the through aperture is formed by excimer laser. Deposition of doped silicon by sputtering is a very slow process taking several days. To be economical a large number of these very small orifice members must be sputter coated simultaneously.

Another construction uses polymer, ceramic, or other suitable material possessing an open pore structure with a high volume porosity, preferably exceeding 90%. These pores will fill with the particle suspending electrolyte but are too small for any particles to enter. The result is a conducting structure with a resistivity about 10% greater than that of the electrolyte. This design has the advantage of being self-adjusting for various electrolyte resistivities. It has the disadvantage that the porous structure is fragile and that cleaning of the porous surface may be required.

Figure 7:
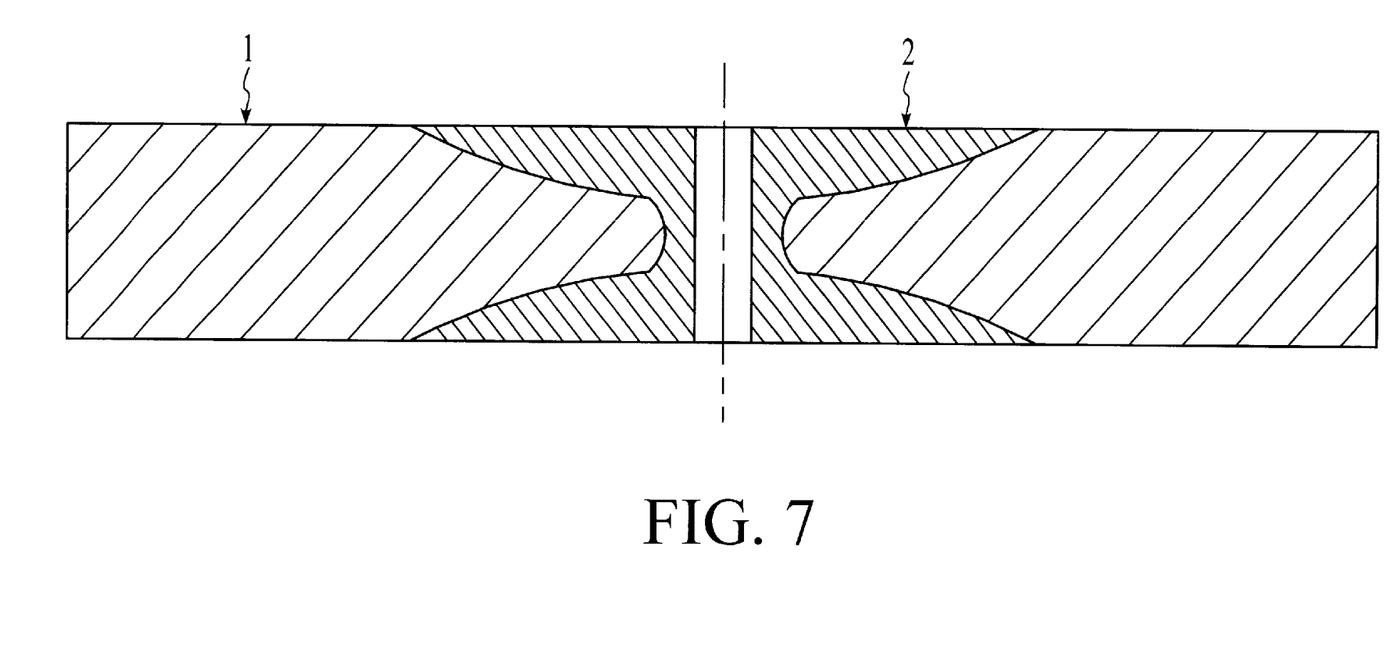
FIG. 7 Practical construction of the particle volume sensing orifice arrangement.

A version similar to FIG. 7 could be made with electrically resistive material on one side only of the orifice member and with D equal to or slightly smaller than d. When used on the orifice member outlet side this electrically resistive material eliminates artifacts due to recirculating particles and the need for rear sheath flow. If the orifice inlet is well rounded there is no need for front sheath flow either.

I claim:

1. An apparatus for counting and sensing the volume of particles by the Coulter method comprising vacuum means to move particles suspended in an electrolyte through an orifice of predetermined diameter having rounded entry and exit corners in an electrically insulating material and with an electrode in contact with said electrolyte before said orifice and a second electrode in contact with said electrolyte after said orifice used to pass a constant electric current through said orifice and having an amplifier to increase the voltage pulse produced across said electrodes by the passage of said particles through said orifice wherein the improvement comprises the following:

(a) electrically resistive material disposed before, within, and after said orifice wherein said orifice entry and exit corners are rounded with a radius of up to one half of said orifice axial length whereby the electric field strength across the minimum diameter of said orifice is substantially uniform thereby permitting use of a diameter of a conduit approximately equal to the minimum diameter of said orifice;

(b) a conduit of predetermined diameter passing through said electrically resistive material approximately concentric with said orifice wherein the corners of said conduit inlet and outlet are approximately 90 degrees and have a corner/radius less than 10% of the radius of said conduit;

(c) said electrically resistive material having an electrical resistivity approximately equal to the electrical resistivity of said electrolyte, whereby all said particles passing through said conduit are guided through a region of substantially identical maximum electric field strength thereby producing substantially identical maximum said voltage pulses for substantially identical said particles and whereby said particles which recirculate downstream of said conduit produce effectively negligible said voltage pulses.

2. The improvement of claim 1 wherein said electrically resistive material is selected from the group consisting of conducting glass, carbon particles dispersed in a rigid polymer matrix, and doped silicon.

3. An apparatus for counting and sensing the volume of particles suspended by the Coulter method comprising means to move particles suspended by the Coulter method comprising vacuum means to move particles suspended in an electrolyte through an orifice of predetermined diameter having rounded entry and exit corners in an electrically insulating material and with an electrode in contact with said electrolyte before said orifice and a second electrode in contact with said electrolyte after said orifice used to pass a constant electric current through said orifice and having an amplifier to increase the voltage pulse produced across said electrodes by the passage of said particles through said orifice wherein the improvement comprises the following:

(a) electrically resistive material disposed within, and after said orifice wherein said orifice entry and exit corners are rounded with a radius of up to one half of said orifice axial length whereby the electric field strength across the minimum diameter of said orifice is substantially uniform thereby permitting use of a diameter of a conduit approximately equal to the minimum diameter of said orifice;

(b) a conduit of predetermined diameter passing through said electrically resistive material approximately concentric with said orifice wherein the corners of said conduit inlet and outlet are approximately 90 degrees and have a corner/radius less than 10% of the radius of said conduit;

(c) said electrically resistive material having an electrical resistivity approximately equal to the electrical resistivity of said electrolyte, whereby all said particles passing through said conduit are guided through a region of substantially identical maximum electric field strength thereby producing substantially identical maximum said voltage pulses for substantially identical said particles and whereby said particles which recirculate downstream of said conduit produce effectively negligible said voltage pulses.

4. The improvement of claim 3 wherein said electrically resistive material is selected from the group consisting of conducting glass, carbon particles dispersed in a rigid polymer matrix, and doped silicon.

* * * * *